United States Patent [19]

Alexander

[11] Patent Number: 5,684,018

[45] Date of Patent: Nov. 4, 1997

[54] ACYLOXYISOPROPYL CARBAMATES AS PRODRUGS FOR AMINE DRUGS

[75] Inventor: Jose Alexander, Lawrence, Kans.

[73] Assignee: Merck & Co., Inc., Rahway, N.J.

[21] Appl. No.: 354,981

[22] Filed: Dec. 13, 1994

[51] Int. Cl.$^6$ .................. A61K 31/455; A61K 31/27; C07D 211/40; C07D 271/16

[52] U.S. Cl. .................. 514/316; 514/487; 546/188; 558/271; 558/272; 558/273; 560/29; 560/32; 560/33

[58] Field of Search .................. 560/29, 33, 32; 546/188; 558/271, 272, 273; 514/316, 487

[56] References Cited

U.S. PATENT DOCUMENTS 4,760,057  7/1988  Alexander .................. 548/146
4,916,230  4/1990  Alexander .................. 548/531

OTHER PUBLICATIONS

Miyauchi et al., Chem. Pharm. Bull.; 38, pp. 1077–1078 (1990).

Saari et al., J. Med. Chem.; 27, pp. 713–717 (1984)).

Sakamoto et al., Chem. Pharm. Bull.; 33, pp. 4870–4877 (1985).

*Primary Examiner*—Bernard Dentz
*Attorney, Agent, or Firm*—Elliott Korsen; Mark R. Daniel

[57] ABSTRACT

This invention relates to novel acyloxyisopropyl carbamates as bioreversible prodrug moieties for amino drugs and to methods of synthesizng these compounds.

12 Claims, No Drawings

ACYLOXYISOPROPYL CARBAMATES AS PRODRUGS FOR AMINE DRUGS

BACKGROUND OF THE INVENTION

This invention relates to the use of acyloxyisopropyl carbamates which are useful in the production of neutral prodrugs from primary and secondary amine drugs as well as the method of synthesis of said prodrugs.

A prodrug is a derivative of a functional drug which, when administered to a warm-blooded animal, "cleaves" in such a manner as to release the drug in its active form at its target site or sites of activity. The enzymatic and/or chemical hydrolytic "cleavage" of the compound occurs in a manner such that the drug is released while the remaining "cleaved" promoiety remains non-toxic and is metabolized in such a manner that non-toxic, metabolic products are produced.

Pharmaceutically active compounds which are also known as drugs or pharmaceuticals, which are amines or have an amine function therein can undergo protonation at physiological pH and are not always transported optimally through biological membranes in the body. For compounds which ionize, the rate of transport through biomembranes appears to be proportional to the concentration of undissociated molecules in solution and the lipid solubility.

It is often advantageous to perform derivatization of the polar amino groups to aid absorption, since this could make the compounds neutral, or more hydrophobic and hence more lipid soluble. Carbamylation confers such properties to amines since carbamates do not ionize at physiological pH. However, success with carbamate ester latentiation requires that it must be hydrolyzed to carbamic acid and the alcohol moiety after penetration through the biological barrier. This is especially true of carbamates of secondary amines in which rates of hydrolysis are $10^5$ to $10^9$ times slower than that of the corresponding primary amines. In this regard, there does not appear to be a carbamate ester specific hydrolytic enzyme in mammals. Though cholinesterase hydrolyze carbamates and become reversibly inhibited in the process, the rates are too slow for practical use. Hence, modified carbamates with an enzymically hydrolyzable ester function were designed as prodrugs for amines by Alexander (U.S. Pat. No. 4,760,057). Esterase catalyzed hydrolysis of the ester moiety triggers the regeneration of the parent amine from such derivatives as depicted below.

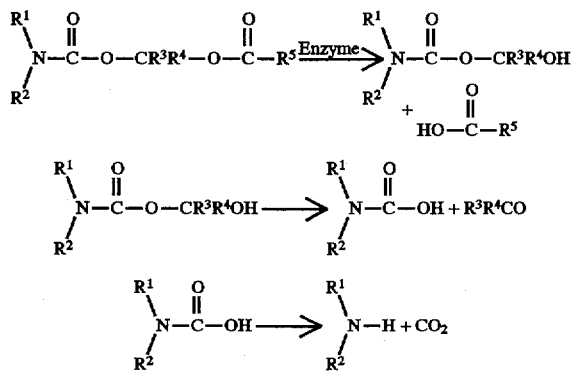

Acyloxyalkyl esters, carbonates and carbamates have been in use as prodrugs for carboxylic acids, alcohols and amines for over three decades. The alkyl portion of these ester esters were derived from either formaldehyde or acetaldehyde and would regenerate these aldehydes on hydrolytic breakdown of the prodrugs. Generation of formaldehyde is considered undesirable because of its perceived toxicity. Although acetaldehyde is considered acceptable from the toxicity point of view, the use of acetaldehyde acetal ester as a prodrug group results in the generation of a chiral center in the prodrug moiety. This would result in the formation of a mixture of diastereoisomers when a chiral molecule is convened to an acyloxyethyl derivative. The diastereoisomers often have a tendency to interact differentially with hydrolytic enzymes, which are chiral.

The susceptibility for enzymatic hydrolysis of these diastereoisomers could be different and hence they could hydrolyze at widely different rates to regenerate the parent drag. Therefore, there is a need for a prodrug strategy that would confer bioreversibility and neutrality to the prodrug at physiological pH and at the same time would not introduce additional chiral centers in the prodrug, or generate undesirable side products.

2-Oxo-1,3-dioxolenylmethyl esters of carboxylic acid with the structure below, have been used as prodrugs for a variety of carboxyl-containing drags. (Miyauchi, et al., Chem. Pharm. Bull. 1990, 38, 1077–1078; Saari, et al., J. Med. Chem., 1984, 27, 713–717.)

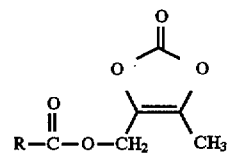

where R is a drag containing a carboxylic acid group. 5-Alkyl-2-oxo-1,3-dioxo-4-ylmethyl esters have been extensively investigated as prodrugs for carboxylic acid groups on B-lactam s antibiotics of the penicillin, cephalosporin and thienamyein class of drags. Lenampicillin (Ikeda, et al., J. Antibiotics, 1984, 32, 4316) is an orally active ampicillin prodrug using this prodrug group. The 2-oxo-1,3-dioxolenylmethyl group has also been used as a prodrug moiety on the amino group of amino functional drugs as shown below (Sakamoto, et al., Chem. Pharm. Bull., 1985, 33, 4870–4877.)

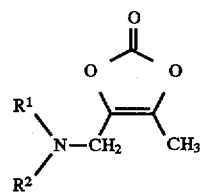

where $R^1R^2N$ is a drug containing an amino group. It has been used to alkylate the piperazino nitrogen in norfloxacin (Sakamoto, et al., Chem. Pharm. Bull., 1985, 33, 4870). The alkylated nofloxacin regenerated the parent drag on oral administration to rats.

The direct alkylation of the amino group with the oxodioxolenylmethyl functionality as above gives a substituted amine that can undergo protonation and is still ionizable. That is, the ionizationality and the hydrophilic nature of the amino group or solubility property of the prodrug is not significantly changed by this type of modification.

Copending U.S. Ser. No. 08/276,220 filed Jul. 18, 1994, discloses novel dioxolenylmethyl carbonate derivatives which are used as starting materials for the one-step synthesis of bioversible oxodioxolenylmethyl carbamate prodrug moieties for drugs or medicaments having primary or secondary amine functions thereon.

U.S. Pat. No. 4,916,230 discloses a method of making carbamates derived from formaldehyde and acetaldehyde derived acetal esters.

U.S. Pat. No. 4,760,057 discloses alkylated compounds prepared by a two-step process which involves treating a primary or secondary amine with an alpha-haloalkyl haloformate to give an alpha-haloalkyl carbamate followed by displacement of the halogen with an acyloxy group by treatment with a metal salt of the carboxylic acid. The metal ion used can be an alkali or alkaline earth metal or a metal such as silver, mercury, and the like. However, there are instances where the application of the disclosed method could result in poor yields as a result of side reactions. For example, silver salts could interact with a free thiol function or mercury salts could give rise to mercuration of highly activated aromatic rings and double bonds.

A ketal ester derived from a symmetrical ketone, such as acetone would alleviate the problem of asymmetry in the prodrug moiety. From the toxicity point of view, acetone is very attractive and a ketal ester prodrug derived from acetone was desired for a long time. But because of synthetic difficulties, a ketal ester prodrug derived from acetone was not accessible.

The problem associated with the generation of an acetone ketal ester in the past was that the displacement of a tertiary halide (most often bromide or iodide) at the isopropyl carbon, with alkali metal or tertiary amine salts of a carboxylic acid, was unsuccessful because of preferential elimination of hydrogen halide.

Therefore, there exists a need for a prodrug forming mechanism that will result in derivatives of primary or secondary mines which are less susceptible to ionization at physiological pH and are free from the side reactions already discussed.

The use of a mercury salt of the carboxylic acid for the displacement reaction, in the present case, alleviated the problem of hydrogen halide elimination and resulted in the successful formation of the acetone ketal ester.

This invention provides a novel method of synthesis of bioreversible prodrug moieties for drugs or medicaments which are suitable for the latentiation of primary and secondary amine drugs. Although acyloxyalkyl carbamates carrying the isopropyl ketal ester have been routinely claimed in the patent art, their preparation has never been disclosed or claimed. This invention also provides the novel acyloxyisopropyl carbonate derivatives which are useful as starting materials for the one-step synthesis.

SUMMARY OF THE INVENTION

There are disclosed acyloxyisopropyl carbamates of the formula (I)

$$R_2R_3N(CO)-O-C(CH_3)_2-O-(CO)-R_1; \quad (I)$$

wherein
R$_2$R$_3$N represents a primary or secondary amine pharmaceutical; and R$_2$ and R$_3$ are the same or different or may be combined to form a cyclic secondary amine; and
R$_1$ is selected from the group consisting of C$_{1-20}$ alkyl, C$_{2-20}$ alkenyl, C$_{2-20}$ alkynyl, aryl, C$_{7-10}$ aralkyl, C$_{3-8}$ cycloalkyl, C$_{3-10}$ cycloalkenyl, C$_{2-20}$ carboxylalkyl, carboxy C$_{5-20}$ cycloalkyl, C$_{2-20}$ haloalkyl, C$_{1-5}$ alkoxycarbonyl C$_{2-10}$ alkyl, C$_{2-20}$ alkylsulfoxide, C$_{2-20}$ carbamyl substituted alkyl, C$_{2-20}$ carbamyl substituted aralkyl, and saturated or unsaturated mono- or polyheterocyclics having from 1 to 3 rings having one or more hetero atoms.

There is also disclosed a process for preparing these compounds as well as compositions containing these compounds.

Throughout the specification and appended claims, the following definitions shall apply unless indicated otherwise.

The term alkyl shall mean a straight or branched chain group having from 1 to 20 carbon atoms, e.g., methyl, ethyl, n-propyl, iso-propyl, n-butyl, t-butyl, and straight or branched chain pentyl and hexyl.

The term aryl shall mean groups carrying an aromatic or substituted aromatic ring such as phenyl, anisyl, toluyl and the like. The contemplated substituents include alkyl, alkoxy, halogen, trifluoromethyl, and the like.

The term halogen shall mean fluorine, chloro, bromine or iodine.

For the purposes of this specification, the term "prodrug" denotes a derivative of a known and proven primary or secondary amino functional drag (e.g. timolol, methyldopa, thiabendazole, etc.) which derivative, when administered to a warm-blooded animal, "cleaves" in such a manner as to release the proven drug form at its target site or sites of activity. The enzymatic and/or chemical hydrolytic "cleavage" of the compounds of the instant invention occurs in a manner such that the proven drug form is released while the remaining "cleaved" moiety remains non-toxic and is metabolized in such a manner that non-toxic, metabolic products are produced.

DETAILED DESCRIPTION OF THE INVENTION

This invention relates to novel acyloxyisopropyl carbamates as prodrugs for amino drugs. In particular, prodrugs of the general formula (I):

$$R_2R_3N-(CO)-O-C(CH_3)_2-O-(CO)-R_1 \quad (I)$$

wherein
R$_2$R$_3$N represents a primary or secondary amine pharmaceutical; and R$_2$ and R$_3$ are the same or different or may be combined to form a cyclic secondary amine;
R$_1$ is selected from the group consisting of C$_{1-20}$ alkyl, C$_{2-20}$ alkenyl, C$_{2-20}$ alkynyl, aryl, C$_{7-10}$ aralkyl, C$_{3-8}$ cycloalkyl, C$_{3-10}$ cycloalkenyl, C$_{2-20}$ carboxylalkyl, carboxy C$_{5-20}$ cycloalkyl, C$_{2-20}$ haloalkyl, C$_{1-5}$ alkoxycarbonyl C$_{2-10}$ alkyl, C$_{2-20}$ alkylsulfoxide, C$_{2-20}$ carbamyl substituted alkyl, C$_{2-20}$ carbamyl substituted aralkyl, and saturated or unsaturated mono- or polyheterocyclics having from 1 to 3 rings having one or more hetero atoms.

This invention also relates to a process for preparing compounds of formula (I)

which comprises reacting a drug, pharmaceutical or medicament with a compound of the formula (II):

$$X-O-(CO)-O-C(CH_3)_2-O-(CO)-R_1 \quad (II)$$

wherein
X is phenyl substituted with at least one substituent selected from the group consisting of nitro, halo, cyano, C$_{1-6}$ alkylsulfonyl, C$_{1-6}$ alkylsulfenyl, trihalomethyl, trihalomethylthio, trihalomethylsulfonyl and trihalomethylsulfenyl or a radical selected from the group consisting of C$_{1-5}$ polyhaloalkyl and C$_{2-12}$ alkylsulfonylalkyl; and
R$_1$, R$_2$ and R$_3$ are as previously defined,
in the presence of a polar aprotic solvent and optionally a catalyst at a temperature ranging from 0° C. to 100° C.

The novel compounds of formula (II) are also disclosed.
The method of synthesizing the novel prodrugs of the invention is illustrated below.

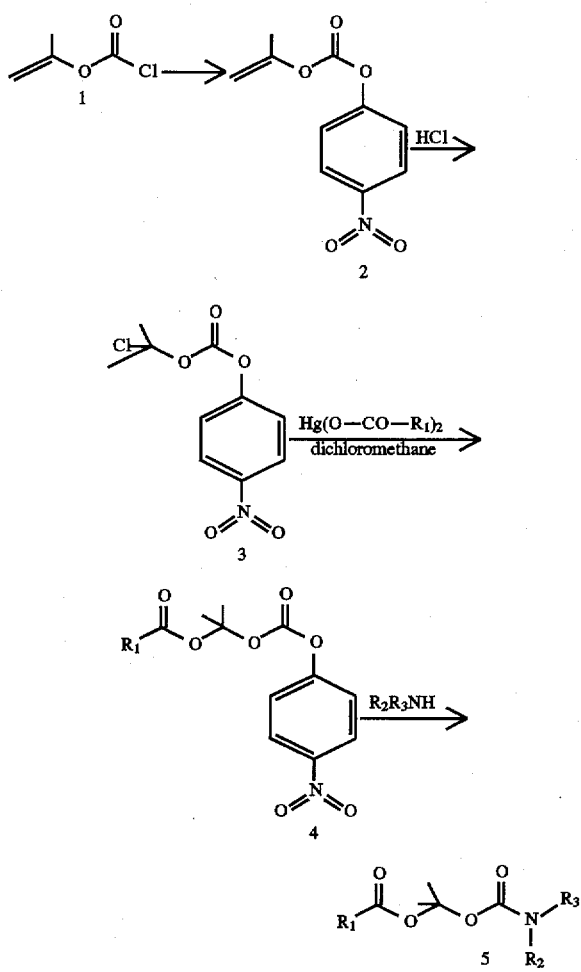

Compound 1, isopropenyl chloroformate, is convened to Compound 2, isopropenyl p-nitrophenyl carbonate by reaction with p-nitrophenol. Compound 2 is subsequently reacted with HCl to form Compound 3, 2-chloro-isopropyl p-nitrophenyl carbonate.

Compound 3 is reacted with a suitable mercury salt of a carboxylic acid, such as mercuric acetate, mercuric propionate, mercuric hexanoate or mercuric benzoate, to displace the chloride and form Compound 4, acyloxyisopropyl p-nitrophenyl carbonate. Compound 4 is reacted with an amine of the formula $R_2R_3NH$, to displace the p-nitrophenyl group and afford Compound 5, the acyloxyisopropyl carbamate of the amine.

Compound 1 is converted to the carbonate by reaction with p-nitrophenol or other suitable agent at a temperature of about 0 to 100° C. for 0.5 to 24 hours.

Compound 2 is reacted with HCl at a temperature of about −20° to 50° C. to form the 2-chloro carbonate.

Compound 4 is formed by displacement of the chloride using a mercury salt of the carboxylic acid in the presence of dichloromethane or other suitable solvent. A catalyst such as 1-hydroxybenzotriazole, imidazole, pyrazole and 1,2,4-triazole may be employed in this step The mercury salt is used to alleviate a problem associated with the use of alkali metal or tertiary amine salts of the carboxylic acid. These salts would preferentially eliminate the hydrogen halide from the tertiary position at the isopropyl carbon. It has been found that this problem can be alleviated by use of a mercury salt. Finally, Compound 4 is reacted with an amine to afford the acyloxyisopropyl carbamate. This reaction takes place in the presence of a polar aprotic solvent such as dimethylformamide, dimethylacetamide, hexamethylphosphorictriamide at a temperature of about 0° C. to 50° C. for 1 to 48 hours. The preferred solvent is dimethylformamide.

As noted above, $R_2R_3N$, can represent any drag, pharmaceutical or medicament having a primary or secondary amine function thereon. Typical drugs, pharmaceuticals or medicaments which can be used and which have the appropriate functionalities thereon include timolol, thiabendazole, norfloxacin, dimethoxyphenethylamine, propanolol, atenolol, pindolol and N-[3(R)-[2-(piperidin-4-yl)ethyl]-2-piperidon-1-yl]acetyl-3(R)-methyl-β-alanine.

Some other drugs, pharmaceuticals or medicaments which can be used and contain the above mentioned functions are listed below. Those skilled in the art will realize that the list is not exclusive and the invention is applicable to other drugs containing primary and secondary amine functions as well.

Those drugs, pharmaceuticals or medicaments containing primary and secondary amines such as timolol: acebutalol, albuterol, alprenolol, atenolol, bucindolol, bunolol, butopamine, butoxamine, carbuterol, cartelolol, colterol, deterenol, dexpropranolol, diacetolol, dobutamine, exaprolol, fenoterol, fenyripol, labotolol, levobunolol, metolol, metaproterenol, metoprolol, nadolol, exprenolol, pamatolol, penbutalol, pindolol, pirbuterol, practolol, prenalterol, primidolol, prizidilol, procaterol, propranolol, quinterenol, rimiterol, ritodrine, sotolol, soterenol, sulfinolol, sulfonterol, suloctidil, tazolol, terbutaline, tiprenolol, tipropidil, tolamolol, thiabendazole, albendazole, albutoin, alinidine, alizapride, miloride, aminorex, aprinocid, cambendazole, cimetidine, clonidine, cyclobendazole, etintidine, fenbendazole, fenmetazole, flubendazole, fludorex, obendazole, mebendazole, metazoline, nocodazole, oxfendazole, oxibendazole, oxmetidine, parbendazole, ranitidine, tetrahydrazoline, tiarnenidine, tinazoline, tiotidine, tolazoline, tramazoline, xylometazoline, dimethoxyphenethylmine: adrenelone, aletamine, amidephrine, amphetamine, aspartame, bamethan, betahistine, clorprenaline, chlortermine, dopamine, etryptamine, fenfluramine, norepinephrine, tocainide, etc.

Other drugs are acyclovir, enviroxime, nifedipine, nimodipine, triamterene, vidarabine, methyldopa, epinephfine and those structurally similar to noffloxacin such as pipemidic acid, 1-ethyl-6-fluoro- 1,4-dihydro-4-oxo-7-(1-piperazinyl)-1,8-naphthyridine-3- carboxylic acid and 1-cyclopropyl-6-fluoro-1,4-dihydro-4-oxo-7-(1-piperezinyl)-3-quinolinecarboxylic acid.

The prodrug compounds can be used to treat any condition for which the parent drug, medicament or pharmaceutical is useful. For example, if timolol is the parent drug of choice, the prodrug can be used for any condition or treatment for which timolol would be administered. Thus, the prodrug compounds of this invention may be administered orally, topically, parentally, by inhalation spray or rectally in dosage unit formulations containing conventional, non-toxic pharmaceutically acceptable carriers, adjuvants and vehicles.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the an for the manufacture of pharmaceutical compositions and such compositions may contain one or more agents selected from the group consisting of sweetening agents, flavoring agents, coloring agents and preserving agents in order to provide pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, maize starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions usually contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and hexitol such as polyoxyethylene sorbitol mono-oleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoate; one or more coloring agents; one or more flavoring agents; and one or more sweetening agents such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present. The pharmaceutical compositions of the invention may also be in the form of oil-in-water emulsions. The oily phase may be a vegetable oil, for example, olive oil or arachis oils, or a mineral oil, for example, liquid paraffin or mixtures thereof. Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may be a sterile injectable solution or suspension in a non-toxic parenterally-acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectibles.

The compounds of the above formula may also be administered in the form of suppositories for rectal administration of the drug. These compositions can be prepared by mixing the drug with a suitable non-irritating excipient which is solid at ordinary temperatures but liquid at the rectal temperature and will therefore melt in rectum to release the drug, for example, cocoa butter and polyethylene glycols.

For topical use, creams, ointments, jellies, solutions, suspensions oil the like containing the prodrugs are employed according to methods recognized in the art. Naturally, the therapeutic dosage range for the compounds of the invention will vary with the size and needs of the patient and the particular pain or disease symptom being treated. However, generally speaking, the following dosage guidelines will suffice. Orally, the therapeutic dose required for a compound of the invention will generally, on a molecular basis, mimic that for the parent primary or secondary amine drug. On a topical basis, application of from about 0.01% to about 2.5% concentration of a compound of the invention (in a suitable topical carrier material) to the affected site should suffice.

The amount of active ingredient that may be combined with the carrier materials to produce a single dosage form will vary depending upon the host treated and the particular mode of administration. For example, a formulation intended for the oral administration of humans may contain from about 5 mg to about 5 gm of active agent compounded with an appropriate and convenient amount of carrier material which may vary from about 5 to about 95 percent of the total composition. Other dosage forms such as ophthalmic dosage forms contain less active ingredient such as for example from about 0.1 mg to about 5 mg. Dosage unit forms will generally contain between from about 0.1 mg to about 1 g of active ingredient. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples are for illustrative purposes only and are not to be construed as limiting the invention disclosed herein.

EXAMPLE 1

Isopropenyl p-nitrophenyl carbonate

Isopropenyl chloroformate (5.0 g) was added to an ice cold suspension of p-nitrophenol in chloroform (100 mL). To the stirred reaction mixture, pyridine (3.32 g) was added dropwise over 20 minutes. After stirring at ice bath temperature for 15 minutes, the reaction mixture was allowed to warm up and stirred at room temperature overnight. The reaction mixture was washed with water, 1N HCl, ice-cold 1% aqueous sodium hydroxide, water and brine. The organic layer was dried over sodium sulfate and evaporated. The solid residue weighed at 8.7 g. It was crystallized from benzene-hexane m.p. 71–72°. $^1$H NMR (CDCl$_3$) δ 2.05 (3H, s), 4.82 (2H, s), 7.44 (2H, d) and 8.01 (2H, d); $^{13}$C NMR (CDCl$_3$) δ19.59, 102.49, 128.25, 128.79, 131.29, 139.8, 153.07 and 163.84; 1R (KBr) 1770, 1521, 1352, 1266, 1207, 859 cm−1.

EXAMPLE 2

2-Chloroisopropyl p-nitrophenyl carbonate

The above isopropenyl carbonate (7.7 g) was dissolved in a mixture of ether (100 mL) and chloroform (100 mL) and cooled in an ice bath under an atmosphere of argon with precaution to exclude moisture. Hydrogen chloride gas was bubbled to saturate the reaction mixture. After allowing to stand at room temperature overnight, the excess HCl gas was removed by bubbling argon. The residual solution was evaporated to remove all the solvent leaving 9.0 g of the product as a solid. $^1$H NMR (CDCl$_3$) δ 2.11 (6H, s), 7.41 (2H, d), and 8.29 (2H, d); $^{13}$C NMR (CDCl$_3$) δ 32.11, 99.75, 121.74, 125.26, 145.51, 148.78 and 155.0; 1R (KBr) 1781, 1557, 1349, 1251, 1220, 1163, 1118 cm$^{-1}$.

EXAMPLE 3

2-Acetoxyisopropyl p-nitrophenyl carbonate

A mixture of 2-chloroisopropyl p-nitrophenyl carbonate (1.0 g) and mercuric acetate (2.0 g) in dichloromethane (100 mL) was stirred at room temperature for 65 hours. The reaction was washed with brine containing a few drops of sodium bicarbonate solution and then with aqueous sodium bicarbonate. The organic layer was dried over sodium sulfate and evaporated to furnish 0.7 g of an oil. $^1$H NMR (CDCl$_3$) δ 1.93 (6H, s), 2.1 (3H, s), 7.39 (2H, d) and 8.28 (2H, d); $^{13}$C NMR (CDCl$_3$) δ21.69, 25.12, 107.43, 121.74, 125.02, 125.1,145.23, 148.73, 155.08 and 168.27.

EXAMPLE 4

N-(Acetoxyisopropoxy)carbonyl-β-(3,4-dimethoxyphenyl)ethylamine

A solution of 3,4-dimethoxyphenethylamine (110 mg) and acetoxyisopropyl p-nitrophenyl carbonate (0.18 g) in dimethylformamide (3 mL) was stirred at room temperature for 18 hours. The reaction mixture was diluted with water (25 mL) and extracted with ethyl acetate. The ethyl acetate extract was washed with water, ice cold 1% aqueous sodium hydroxide, 1N HCl, water and brine. The organic extract was dried over sodium sulfate and evaporated. The residue (0.11 g) was purified by preparative thin layer chromatography on silica gel plates. The title compound (75 mg) was eluted with ethyl acetate-chloroform (5:95). $^1$H NMR (CDCl$_3$) δ 1.81 (6H, s), 2.05 (3H, s), 2.75 (2H, t), 3.36 (2H, m), 4.85 (1H, br, t), 6.71–6.84 (3H, m); $^{13}$C NMR (CDCl$_3$) δ 22.05, 25.9, 35.45, 41.91, 55.76, 55.83, 105.07, 111.29, 111.87, 120.61, 131.09, 147.59, 148.91, 153.36 and 168.79; 1R (film) 3370, 2941, 1748, 1718, 1517, 1464, 1370, 1261, 1238, 1140, 1027 cm$^{-1}$; HRMS (e/m) calculated for C$_{16}$H$_{23}$NO$_6$, 325.1525; found, 325.1512.

EXAMPLE 5

{3(R)-2-{1-[2(Acetoxy) isopropoxycarbonylpiperidine- 4yl]-ethyl } piperidone-1}-acetyl-3(R)-methyl-β-alanine A mixture of [3(R)-2-piperidine-4yl-ethyl)-2-piperidone-1]-acetyl-3(R)-methyl-β-alanine (200 mg) and acetoxyisopropyl p-nitrophenyl carbonate (240 mg) was stirred in dimethylformamide (5 mL) at room temperature for 18 hours. The dimethylformamide was evaporated in vacuo. The residue was taken in water and extracted with ethyl acetate. The organic extract was washed with water, aqueous 1N HCl, water and brine, dried over sodium surf ate and evaporated to furnish 0.34 g of a residue. The residue was purified by chromatography over Sephadex LH-20 and the pure acetoxyisopropyl carbamate was eluted with chloroform as an oil (190 mg). $^1$H NMR (CDCl$_3$) δ 1.0–2.1 (13H, m), 1.23 (3H, d), 1.83 (6H, s), 2.04 (3H, s), 2.35 (1H, m), 2.52 (2H, m) 2.72 (2H, m), 3.42 (2H, m), 3.97 (2H, q), 4.35 (1H, m), 7.1 (1H, d); $^{13}$C NMR (CDCl$_3$) δ 19.87, 21.42, 22.13, 25.99, 28.82, 31.8, 32.09, 33.51, 35.97, 39.61, 41.40, 41.95, 43.93, 44.52, 49.83, 51.89, 105.37, 152.39, 168.16, 168.88, 173.91, 174.07.

EXAMPLE 6

Benzoyloxyisopropyl p-nitrophenyl carbonate

A suspension of mercuric oxide (2.16 g) and benzoic acid (2.44 g) in dichloromethane (150 mL) was stirred at room temperature until the mercuric oxide was completely converted to mercuric benzoate. 2-Chloroisopropyl p-nitrophenyl carbonate (2.8 g) was added to the suspension of mercuric benzoate and the reaction mixture was stirred at room temperature for 24 hours. The solution was washed with saturated aq. sodium chloride solution, aq. sodium bicarbonate, water and brine. Evaporation of the solvent gave 2.18 g of an oily residue. The crude compound was purified by preparative thin layer chromatography on silica gel plates on a Chromatatron® yielding 1.86 g of the compound as a viscous liquid following elution with chloroform. $^1$H NMR (CDCl$_3$) δ 2.09 (6H, s), 7.4–7.65 (5H, m), 8.03 (2H, d), 8.27 (2H, d); $^{13}$C NMR (CDCl$_3$) 25.42, 108.16, 121.83, 125.24, 128.45, 129.8, 129.98, 133.49, 145.37, 148.99, 155.22 and 163.82.

EXAMPLE 7

{3(R)-2-{1-[(2(Benzoyloxy)isopropylcarbonyl) piperidine-4yl]-ethyl }piperidone-1}-acetyl-3(R)-methyl-β-alanine A mixture of [3(R)-(2-piperidine-4yl-ethyl)-2-piperidone-1]-acetyl-3(R)-methyl-β-alanine (353 mg) and benzoyloxyisopropyl p-nitrophenyl carbonate (380 mg) in DMF (10 mL) was stirred at room temperature for 18 hours. The reaction mixture was diluted with 50 mL water and extracted with ethyl acetate. The ethyl acetate extract was washed with water and brine, dried over sodium sulfate and evaporated. The liquid residue (0.74 g) was purified by chromatography over Sephadex LH-20. The pure benzoyloxyisopropyl carbamate (0.4 g) was eluted with chloroform. $^1$H NMR (CDCl$_3$) δ 1.0–2.1 (3H, m), 1.22 (3H, d), 1.98 (6H, s), 2.35 (1H, m), 2.49 (2H, d), 2.75 (2H, br), 3.97 (2H, q), 4.13 (2H, m), 4.3 (1H, m), 7.05 (1H, d), 7.3–7.7 (3H, m) and 7.95–8.05 (2H, m); $^{13}$C NMR (CDCl$_3$) δ 19.76, 21.23, 25.85, 25.93, 28.05, 31.69, 31.95, 33.38, 35.78, 39.68, 41.20, 41.96, 43.79, 44.48, 49.59, 51.48, 105.85, 128.11, 129.54, 130.73, 132.73, 152.26, 163.99, 168.05, 173.74 and 173.94.

EXAMPLE 8

2-Hexanoyloxyisopropyl p-nitrophenyl carbonate

A suspension of mercuric oxide (2.16 g) in hexanoic acid (4.64 g) was stirred at room temperature for one hour. Dichloromethane (10 mL) was added and stirring continued for an additional hour. Chloroisopropyl p-nitrophenyl carbonate (2.6 g) and dichloromethane (60 mL) were added and stirred at room temperature for 16 hours. The reaction mixture was washed successively with saturated aq. NaCl, aq. sodium bicarbonate and brine. The mixture was dried over sodium sulfate and evaporated to furnish 2.14 g of an oil. $^1$H NMR (CDCl$_3$) δ 0.90 (3H, m), 1.34 (6H, m), 1.63 (2H, m), 1.93 (6H, s), 2.54 (2H, s), 7.38 (2H, d) and 8.28 (2H, d).

EXAMPLE 9

{3(R)-2-{1-[2(Hexanoyloxy)isoproylcarbonyl] piperidine-4yl}-ethyl}piperidone-1-(3R)-methyl-5-ketopentanoic acid A mixture of [3(R)-2-(piperidine-4-ylethyl)-2-piperidine-2-[(3R)-methyl-5-ketopentanoic acid](350 mg) and hexanoyloxyisopropyl p-nitrophenyl carbonate (400 mg) in DMF (5 mL) was stirred at room temperature for 16 hours. The ethyl acetate extract was washed with water and brine, dried over sodium sulfate and evaporated. The residue (0.75 g) was purified by preparative thin layer chromatography over silica gel. $^{13}$C NMR (CDCl$_3$) δ 13.81, 13.85, 19.90, 21.43, 22.24, 24.37, 24.43, 26.03, 28.83, 31.12, 31.18, 31.82, 32.11, 33.55, 35.11, 35.97, 39.82, 41.41, 42.02, 43.95, 44.55, 49.74, 51.89, 105.29, 152.42, 168.30, 171.66, 174.13, 175.24, 179.04.

EXAMPLE 10

Regeneration of the parent drug by rat plasma hydrolysis of the prodrug

The rate of hydrolysis of the acetoxyisopropyl carbamate prodrug of [3(R)-2-(piperidine-4-yl)ethyl]-2-piperidone-1-[(3R)-methyl-5-ketopentanoic acid]by plasma enzymes was studied by measuring the formation of the parent amine drug at 37° C. in rat plasma. The reaction was initiated by adding an aqueous solution of the carbamate prodrug to the reaction medium pre-equilibrated at 37° C. in a thermostated water bath. The initial concentration of the prodrug in rat plasma was $6.3 \times 10^{-5}$ M. Samples (100 μl) were withdrawn at intervals and mixed with saturated ammonium sulfate (200 μl), vortex mixed for 10 seconds and centrifuged for 5 minutes at 14,000 g to precipitate plasma proteins. The supernatant was injected directly and analyzed by HPLC on a 20 cm Brownlee Spheri-5 RP-18 column combined with a similar 3 cm guard column. The mobile phase used for the analysis was 0.01M K$_2$HPO$_4$ buffer (adjusted to pH 6.5 with phosphoric acid) containing 3% acetonitrile at a flow rate of 1 mL/min. The retention time under these conditions for the amine drug was approximately 15 minutes. The concentration of the compounds was measured at 210 nm using a variable wavelength. UV detector. The half-life for the hydrolysis of the acetoxyisopropyl carbamate prodrug in rat plasma at 37° C. was 32±6 minutes (n=2).

What is claimed is:

1. A compound of the formula $$R_2R_3N(CO)-O-C(CH_3)_2-O-(CO)-R_1;$$

wherein $R_2R_3N$ represents a primary or secondary amine pharmaceutical; and $R^2$ and $R^3$ are the same or different or may be combined to form a cyclic secondary amine; and $R_1$ is $C_{1-20}$ alkyl, $C_{2-20}$ alkenyl, $C_{2-20}$ alkynyl, aryl, $C_{7-10}$ aralkyl, $C_{3-8}$ cycloalkyl, $C_{3-10}$ cycloalkenyl, $C_{2-20}$ carboxylalkyl, carboxy $C_{5-20}$ cycloalkyl, $C_{2-20}$ haloalkyl, $C_{1-5}$ alkoxycarbonyl $C_{2-10}$ alkyl, $C_{2-20}$ alkylsulfoxide, $C_{2-20}$ carbamyl substituted alkyl or $C_{2-20}$ carbamyl substituted aralkyl, and saturated or unsaturated mono- or polyheterocyclics having from 1 to 3 rings having one or more hetero atoms.

2. A process for preparing a compound as defined in claim 1 wherein $R_2R_3N$ is any drug, pharmaceutical or medicament having a primary or secondary amine function; and $R^2$ and $R^3$ are the same or different or may be combined to form a cyclic secondary amine; and $R_1$ is $C_{1-20}$ alkyl, $C_{2-20}$ alkenyl, alkynyl, aryl, $C_{7-10}$ aralkyl, $C_{3-8}$ cycloalkyl, $C_{3-10}$ cycloalkenyl, $C_{2-20}$ carboxylalkyl, carboxy $C_{5-20}$ cycloalkyl, $C_{2-20}$ haloalkyl, $C_{1-5}$ alkoxycarbonyl $C_{2-10}$ alkyl, $C_{2-20}$ alkylsulfoxide, $C_{2-20}$ carbamyl substituted alkyl or $C_{2-20}$ carbamyl substituted aralkyl, and saturated or unsaturated mono- or polyheterocyclics having from 1 to 3 rings having one or more hetero atoms, which comprises reacting a drug, pharmaceutical or medicament with a compound of the formula:

$$X-O-(CO)-O-C(CH_3)_2-O-(CO)-R_1$$

wherein

X is phenyl substituted with one or more of the substituents selected from the group consisting of nitro, halo, cyano, $C_{1-6}$ alkylsulfonyl, $C_{1-6}$ alkylsulfenyl, trihalomethyl, trihalomethylthio, trihalomethylsulfonyl and trihalomethylsulfenyl or a radical selected from the group consisting of $C_{1-5}$ polyhaloalkyl and $C_{2-12}$ alkylsulfonylalkyl;

in the presence of a polar aprotic solvent and optionally a catalyst at a temperature ranging from 0° C. to 100° C.

3. The process of claim 2 wherein the polar aprotic solvent is selected from the group consisting of dimethylformamide, dimethylacetamide, hexamethylphosphorictriamide, and 1,3-dimethyl-2-imidizolidinone and the catalyst is selected from the group consisting of 1-hydroxybenzotriazole, imidazole, pyrazole and 1,2,4-triazole.

4. The process of claim 3 wherein the reaction takes place within a temperature range of 0° C. to 60° C.

5. A compound of the formula:

$$X-O-(CO)-O-C(CH_3)_2-O-(CO)-R_1$$

wherein

X is phenyl substituted with one or more of the substituents selected from the group consisting of nitro, halo, cyano, $C_{1-6}$ alkylsulfonyl, $C_{1-6}$ alkylsulfenyl, trihalomethyl, trihalomethylthio, trihalomethylsulfonyl and trihalomethylsulfenyl or a radical selected from the group consisting of $C_{1-5}$ polyhaloalkyl and $C_{2-12}$ alkylsulfonylalkyl; and $R_1$ is $C_{1-20}$ alkyl, $C_{2-20}$ alkenyl, $C_{2-20}$ alkynyl, aryl, $C_{7-10}$ aralkyl, $C_{3-8}$ cycloalkyl, $C_{3-10}$ cycloalkenyl, $C_{2-20}$ carboxylalkyl, carboxy $C_{5-20}$ cycloalkyl, $C_{2-20}$ haloalkyl, $C_{1-5}$ alkoxycarbonyl $C_{2-10}$ alkyl, $C_{2-20}$ alkylsulfoxide, $C_{2-20}$ carbamyl substituted alkyl or $C_{2-20}$ carbamyl substituted aralkyl, and saturated or unsaturated mono- or polyheterocyclics having from 1 to 3 rings having one or more hetero atoms.

6. The compound as defined in claim 5 wherein X is halophenyl, nitrophenyl or polyhaloalkyl.

7. The compound as defined in claim 6 wherein X is p-nitrophenyl.

8. A pharmaceutical composition comprising a compound as defined in claim 1 and a pharmaceutically acceptable carrier thereof.

9. The compound of claim 1 wherein the primary or secondary amine is a pharmaceutically active compound.

10. The compound of claim 9 wherein the primary or secondary amine is selected from the group consisting of timolol, thiabendazole, norfloxacin, dimethoxyphenethylamine, propanolol, atenolol, pindolol, methyldopa, epinephrine, dopamine, metoprolol, carteolol, pipemidic acid, N-[3(R)-[2-(piperiden-4-yl)ethyl]-2-piperidon-1-yl]acetyl-3(R)-methyl-β-alanine, acebutalol, albuterol, alprenolol, bucindolol, bunolol, butopamine, butoxamine, carbuterol, colterol, deterenol, dexpropranolol, diacetolol, dobutamine, exaprolol, fenoterol, fenyripol, labotolol, levobunolol, metolol, metaproterenol, nadolol, exprenolol, pamatolol, penbutalol, pirbuterol, practolol, prenalterol, primidolol, prizidilol, procaterol, quinterenol, rimiterol, ritodrine, sotolol, soterenol, sulfinolol, sulfonterol, suloctidil, tazolol, terbutaline, tiprenolol, tipropidil, tolamolol, thiabendazole, albendazole, albutoin, alinidine, alizapride, amiloride, aminorex, aprinocid, cambendazole, cimetidine, clonidine, cyclobendazole, etintidine, fenbendazole, fenmetazole, flubendazole, fludorex, lobendazole, mebendazole, metazoline, nocodazole, oxfendazole, oxibendazole, oxmetidine, parbendazole, ranitidine, tetrahydrazoline, tiamenidine, tinazoline, tiotidine, tolazoline, tramazoline, xylometazoline, adrenelone, aletamine, amidephrine, amphetamine, aspartame, bamethan, betahistine, clorprenaline, chlortermine, etryptamine, fenfluramine, norepinephrine and tocainide.

11. The compound as defined in claim 10 wherein the primary or secondary amine is selected from the group consisting of timolol, thiabendazole, norfloxacin, dimethoxyphenethylamine, propanolol, atenolol, pindolol, methyldopa, epinephrine, dopamine, metoprolol, carteolol, pipemidic acid and N-[3(R)-[2-(piperidin-4-yl)ethyl]-2-piperidon-1-yl]acetyl-3(R)-methyl-β-alanine.

12. A method for alleviating pain or disease symptoms in a warm-blooded animal exhibiting pain or disease symptoms which comprises administering to said animal a pain deviating or anti-disease symptom effective amount of a compound as defined in claim 1.

* * * * *